United States Patent [19]
Bird et al.

[11] Patent Number: 5,646,047
[45] Date of Patent: Jul. 8, 1997

[54] METHOD AND REAGENT KIT FOR DETERMINING PAPER DEGREDATION IN TRANSFORMERS

[75] Inventors: Frederick John Bird, Surrey; Nicola Dominelli, Coquitlam; Gordon R. Ashby, Surrey, all of Canada

[73] Assignee: Powertech Labs Inc., Surrey, Canada

[21] Appl. No.: 575,288

[22] Filed: Dec. 20, 1995

Related U.S. Application Data

[63] Continuation-in-part of Ser. No. 376,490, Jan. 20, 1995, abandoned, which is a continuation-in-part of Ser. No. 139,431, Oct. 20, 1993, abandoned.

[51] Int. Cl.$^6$ ............................................. G01N 33/26
[52] U.S. Cl. .............................. 436/128; 436/56; 436/60; 436/93
[58] Field of Search ........................ 436/60, 56, 93, 436/128, 164; 422/61

[56] References Cited

U.S. PATENT DOCUMENTS

| | | |
|---|---|---|
| 3,761,532 | 9/1973 | De Gramont et al. |
| 4,486,610 | 12/1984 | Lund. |
| 4,514,503 | 4/1985 | Orelup. |
| 4,865,991 | 9/1989 | Mathers. |

*Primary Examiner*—Jill Warden
*Assistant Examiner*—Jan M. Ludlow
*Attorney, Agent, or Firm*—Christie, Parker & Hale, LLP

[57] ABSTRACT

This invention relates to power transformers. More particularly, this invention pertains to a method and apparatus for detecting the degree of degradation of paper insulation in a transformer by determining the concentration of furaldehyde in the transformer oil. A reagent for detecting the presence of furaldehyde in transformer oil comprising: (a) a primary amine selected from the group consisting of aniline, toluidine, anisidine, aminophenol or an amine; (b) a second component having about 3 mL of about 15 to 33 (weight to volume) percent of acetic acid alone, or in combination with citric acid; from about 67 to 85 (volume) percent of a halogenated hydrocarbon selected from the group consisting of dichloromethane, chloroform, carbontetrachloride, dichloroethane, trichloroethane, tetrachloroethane, trichloroethylene, tetrachloroethylene; about 4 (weight to volume) percent of salicylic acid; and about 1 (weight to volume) percent of an anti-oxidant; and (c) a third component having about 1.25 mL of about 25 (weight to volume) percent citric acid in distilled water.

9 Claims, No Drawings

METHOD AND REAGENT KIT FOR DETERMINING PAPER DEGREDATION IN TRANSFORMERS

This is a continuation-in-part of application Ser. No. 08/376,490, filed Jan. 20, 1995, now abandoned, which was a continuation-in-part of application Ser. No. 08/139,431, filed Oct. 20, 1993, now abandoned.

FIELD OF THE INVENTION

This invention relates to power transformers. More particularly, this invention pertains to a method and apparatus kit for detecting the degree of degradation of paper insulation in a transformer by determining the concentration of cellulose breakdown products, and particularly furaldehyde, in transformer oil contained in the transformer.

BACKGROUND OF THE INVENTION

Power transformers, and other large transformers, are a key component of the power transmission system in an electric utility. Several thousand such transformers may be in use at a major facility. A single power transformer may represent an investment of millions of dollars, so a failure can be extremely costly in outage time and investment loss. Transformers are designed to last about 40 years. The residual life of an operating transformer is typically dependent on the residual life of the solid insulation in the transformer.

The solid insulation for the coils in most power transformers and other large transformers is oil impregnated paper. This paper is immersed in a dielectric fluid, such as transformer oil. By monitoring the condition of the paper insulation component it is possible to schedule and minimize maintenance procedures and adjust the power level input in order to extend the useful life of the transformer and reduce maintenance costs.

As the insulation paper ages by thermal degradation (typically, transformers are rated to operate at temperatures between 55° C. and 65° C. above ambient), the cellulose in the paper breaks down. Specific degradation compounds from this breakdown process appear and build up in the transformer oil. The most prominent is a build up of furaldehyde (also known as furfuraldehyde, furfural, fural or 2-furaldehyde) and related furaldehyde such as 5-methyl 2 furaldehyde and 5 hydroxy-2 furaldehyde. By monitoring the amount of furaldehyde build up in the oil, the condition (or proportional degree of degradation) of the paper insulation can be assessed.

The presence of furaldehyde build-up in the insulating oil of transformers as an indicator of paper insulation degradation, has been known for some years. Around 0.1 to 0.5 parts per million of furaldehyde in the oil is the range that is now considered as an indication that cellulose in the paper insulation is degrading at a significant rate. The importance of being able to detect furaldehyde at such low levels is now becoming appreciated by maintenance engineers.

In some power utilities equipped with laboratories, transformer oil samples are routinely monitored for the presence of furaldehyde as an indicator of paper degradation. The conventional procedure employs high performance liquid chromatography (HPLC), which provides comprehensive information on numerous paper degradation products and is sensitive to very low levels of furaldehyde (as low as 0.01 ppm). But the HPLC procedure is slow and expensive and requires a trained technician operator.

The detection of furaldehyde in new, clean petroleum products, which do not have any significant oxidation breakdown products, has been accomplished in the petroleum industry by using an aniline in acetic acid reagent and measuring the colour produced with a photometer, or alternatively by visual examination of the colour in the acetic acid layer which separates out underneath the petroleum product layer. A problem with the acetic acid/aniline test is that the mixture solidifies at about 16° C. Therefore, the test is not useful outdoors in cold climates.

Transformer oil, unlike the clear thin petroleum products that are usually tested with the acetic acid/aniline test, for example, gasoline, kerosene and the like, presents a challenge because transformer oil is viscous which retards reaction rates. Also, transformer oil oxidizes and darkens under use. The transformer oil in a typical transformer may be 5 to 40 years old. Since they operate at elevated temperatures, for example, up to 105° or higher at localized spots, the build-up of oxidation breakdown products can be significant. These breakdown products can form emulsions which interfere with the test. In the case of viscous transformer oil, which retards movement of the acetic acid reagent, a diluent solvent can be used to reduce the viscosity of the oil so that the acetic acid reagent can more effectively contact the furaldehyde in the oil.

To increase the sensitivity of the aniline-acetic acid test, the furaldehyde can be pre-concentrated by extracting a large volume of the oil with a small volume of a suitable solvent. This extracted material is then used for conducting the analysis. This additional step increases the complexity of the procedure and requires a trained technician operator.

Using the alternative photometric colour measurement procedure described is relatively tedious, time consuming and requires a photometer and a trained technician operator. The test is advantageous, however, because when the procedure is used to detect furaldehyde in oxidized transformer oil, a minimum test sensitivity as low as about 0.05 ppm of furaldehyde can be achieved.

Visual colour measurement, if it could be done reliably, is desirable because it is simple, much less tedious, and does not require any instruments or a trained technician operator. But, because it is optical, it is inherently less sensitive. When used to detect furaldehyde in transformer oils, the sensitivity is further reduced because: (a) the use of a diluent solvent reduces the furaldehyde concentration, making detection more difficult, (b) yellowish or brownish coloured oxidation products from the oil are extracted by the acetic acid and these mask the true intensity of the furaldehyde red/pink compound and reduce the visual detection limit of the test, and (c) the oxidation products form emulsions which obscure the distinction between the upper oil layer and the lower pink/red coloured layer.

To date, the minimum test sensitivity of visual colour detection of furaldehyde in transformer oil, without resorting to an additional pre-concentration step, has only been about 0.5 to 1.0 ppm of furaldehyde depending on the colour condition (oxidation level) of the oil. The visual test is therefore not sufficiently sensitive to enable a meaningful paper degradation assessment to be carried out, particularly under cold field conditions. As mentioned before, a serious problem in using an aniline/acetic acid test is that when aniline and acetic acid are mixed, the mixture freezes at +16° C. This limits the applicability of the test in indoor or outdoor conditions when temperatures are below +16° C.

As the significance and usefulness of furaldehyde detection, as evidence of cellulose breakdown, to monitor the condition of paper insulation in transformers and other electrical equipment, has become more appreciated, and hence more important, the demand for analysis has increased substantially. This has led to the need for a simple reliable, accurate test that can be conducted visually in the field by non-chemistry trained personnel to rapidly detect the presence of low levels of furaldehyde in transformer oil that has been in use in transformers for years.

There is, to the applicant's knowledge, no quick and reliable visual field test for detecting low levels of furaldehyde in oxidized viscous transformer oil.

U.S. Pat. No. 4,514,503, issued Apr. 30, 1985, R. B. Orelup, discloses a two-component liquid reagent comprising a first component and a second component for detecting the presence of furfural in new, clear light petroleum products of low viscosity, such as gasoline, kerosene, diesel oil, and the like. Orelup uses diethylene glycol in each component to lower the freezing point of the mixture. The freezing points of the two components are stated to be less than −40° C. Each component of the liquid reagent is stored separately from the other component and both components are combined with each other prior to admixture with the petroleum product. The test is intended for use by tax authorities to monitor unauthorized blending of motor fuels with less expensive products such as low octane gas and heating fuels, the latter having a lesser tax rate.

The two components of Orelup comprise the following compositions on a weight basis:

First Component: (a) from about 15 to about 22 volume percent of a primary amine selected from the group consisting of aniline, meta-aminophenol, para-anisidine, meta-toluidine and para-toluidine; (b) from about 35 to 45 volume percent of diethylene glycol; (c) from about 35 to about 45 volume percent of ethanol; and (d) from about 1 to 2 weight to volume percent of an antioxidant.

Second Component: (a) from about 18 to about 25 weight to volume percent of an acid selected from the group consisting of citric acid, lactic acid, formic acid and phosphoric acid; (b) from about 35 to about 45 volume percent of diethylene glycol; and (c) from about 35 to 45 volume percent of ethanol.

There is a proviso in Orelup that when the amine in the first component is aniline, then the acid in the second component must be an organic acid selected from the group consisting of citric acid, lactic acid and formic acid. This is probably to avoid the high freezing point (+16° C.) of the aniline/acetic acid mixture. The use of diethylene glycol (which is a well known and widely used anti-freeze in sprinkler systems and automotive radiator systems) and ethanol in each component is also taught. It is claimed that this method with no pre-extraction can detect 0.25 ppm of furaldehyde in new clean gasoline, diesel fuel, kerosene, naptha, or heating oil, all of light viscosity.

These light petroleum products are clear in colour and are fresh. They are not old or degraded in any way. They are not heavy hydrocarbons of high viscosity.

The test taught by Orelup produces a petroleum product upper layer and a separated lower layer which displays a red colour if there is a furaldehyde primary amine reaction. The lower indicator layer is prone to interference from emulsions formed by degradation products.

Orelup discloses the presence of inhibiting and diluting diethylene glycol in both the first component and the second component. Orelup also discloses large amounts of diluting ethanol in both the first component and the second component. The presence of additional chemicals in each component dilutes the concentrations and reduces the sensitivity and the reliability of the procedure.

SUMMARY OF THE INVENTION

The present invention provides a novel, portable, field usable, user friendly, three-component reagent for reliably detecting paper degradation levels in transformers by detecting low levels of furaldehyde in degraded viscous transformer oils. The pink/red colour indicative of a furaldehyde primary amine reaction appears in an upper layer which is not interfered with by contaminants in the lower layer containing the separated oil product. The combination of reagents works together to minimize the interference from emulsions caused by oil oxidation products.

The invention pertains to a reagent for determining extent of paper degradation in a transformer containing paper and transformer oil by detecting the presence of furaldehyde in the transformer oil comprising: (a) a first component comprising about 0.1 mL of a primary amine selected from the group consisting of aniline, toluidine, anisidine, aminophenol or an amine; (b) a second component comprising about 3 mL of about 15 to 33 (volume) percent of acetic acid alone, or in combination with citric acid; from about 67 to 85 (volume) percent of a halogenated hydrocarbon selected from the group consisting of dichloromethane, chloroform, carbontetrachloride, dichloroethane, trichloroethane, tetrachloroethane, trichloroethylene, tetrachloroethylene; about 4 (weight to volume) percent of salicylic acid; and about 1 (volume) percent of an anti-oxidant; and (c) a third component comprising about 1.25 mL of about 25 (weight to volume) percent citric acid in distilled water.

The reagent can consist essentially of aniline as the first component; acetic acid, tetrachloroethylene, salicylic acid and t-butyl hydroquinone as anti-oxidant, as the second component; and citric acid in distilled water as the third component.

The invention is also directed to a reagent kit for deterring extent of paper degradation in a transformer by detecting the presence of furaldehyde in about 3 mL of transformer oil, said reagent kit comprising: (a) a sealed pipette containing about 0.1 mL of aniline; (b) a vessel with removable cap comprising about 3 mL of about 15 (volume) percent of acetic acid, about 85 (volume) percent of tetrachloroethylene, about 4 (weight to volume) percent salicylic acid and about 1 (volume) percent antioxidant; and (c) a second sealed pipette containing about 1.25 mL of about 25 (volume) percent citric acid in distilled water.

The aniline in pipette (a) can be absorbed in a substrate and the vessel (b) can be a test tube with a Teflon lined plastic cap. The substrate can be a nylon fabric and the pipettes (a) and (c) can be disposable.

The invention is also directed to a process for determining extent of paper degradation in a transformer containing paper and transformer oil by detecting the presence of furaldehyde in transformer oil containing said furaldehyde comprising: (a) withdrawing about 3 mL of the transformer oil with a pipette containing about 0.1 mL of aniline; (b) adding the 3 mL of transformer oil and the 0.1 mL of aniline contents of the pipette to a transparent vessel containing 3 mL of about 15 weight to volume percent of acetic acid and about 85 volume percent of tetrachloroethylene; (c) adding to the vessel and its contents the contents of a pipette containing 1.25 mL of about 25 weight to volume percent citric acid in distilled water; (d) capping the vessel and shaking the contents of the vessel for a time sufficient to permit the contents to chemically react with one another; (e) observing the intensity of a pink/red colour characteristic of a furaldehyde complex in an upper layer formed on top of the transformer oil mixture; and (f) comparing the intensity of the pink/red colour with the intensity of colour on a calibrated colour standards medium. The pipettes and vessel can be sealed air tight prior to opening.

DETAILED DESCRIPTION OF SPECIFIC EMBODIMENTS OF THE INVENTION

We have invented a portable, reliable, outdoor friendly, easy to use, highly sensitive, three-component chemical reagent kit for the determination of paper breakdown in a transformer by detection of low levels of furaldehyde in degraded transformer oil. The reagents possess the following advantageous characteristics:

1. The three reagents are stored separately to improve stability and shelf life. The colour that is developed in an upper layer when the reagents are used in detecting furaldehyde is stable, does not fade or change, and is less susceptible to contamination from a layer containing petroleum products, than is a lower indicator layer.
2. The test sensitivity is sufficiently great that detection of furaldehyde even in diluted and aged mineral oil can be made by visual means, without pre-concentration steps, in concentrations as low as about 0.1 parts per million of furaldehyde. A comparison of detection limit in viscous transformer oil, which must be diluted, is the most relevant comparison because in diesel and heating oil, a lower furaldehyde detection level is easier to achieve because a diluent solvent is not required, and the diesel or heating oil is not viscous and is a new clean product.
3. Interference from coloured oil oxidation products in the degraded oil and formed emulsions is substantially reduced because the colour indicator appears in an upper layer.
4. The analytical procedure for low level semi-quantitative measurement of furaldehyde in mineral oil is simplified and is much more rapid than prior art tests.
5. The kit and analytical procedure can be used in both indoor and outdoor conditions, even at extremely low temperatures (for example, −40° C.).
6. The reagent components are held in sealed airtight containers which ensure reagent stability, ease of use and operator safety.
7. The volume of transformer oil and reagents required for the test is minimal and therefore a compact, portable multiple sample test kit package is possible.

The subject invention is not anticipated or taught by Orelup because Orelup does not disclose or suggest a small, compact, portable, easy to use three-component sealed liquid reagent kit for use in reliably detecting and determining very low levels of furaldehyde in heavy viscous transformer oil, which may be degraded and extensively darkened due to oxidization. Orelup does not disclose detecting furaldehyde by viewing an upper indicator layer which is less prone to contamination from oxidants. Orelup does not disclose the use of acetic acid, or a chlorinated hydrocarbon such as tetrachloroethylene in a second component.

The three components comprise the following compositions on a weight/volume basis:

(a) First Component 0.1 mL of a primary amine selected from the group consisting of aniline, toluidine, anisidine, aminophenol or an amine;

(b) Second Component 3 mL of (a) about 15 to 33 weight to volume percent of acetic acid alone, or in combination with citric acid; (b) about 67 to 85 volume percent of a halogenated hydrocarbon selected from the group consisting of dichloromethane, chloroform, carbontetrachloride, dichloroethane, trichloroethane, tetrachloroethane, trichloroethylene, tetrachloroethylene; (c) about 4 weight to volume percent of salicylic acid, and (d) about 1 percent of an anti-oxidant, t-butyl hydroquinone.

(c) Third Component 1.25 mL of about 25 weight percent citric acid in distilled water.

In practice, a small amount (typically about 3 ml) of transformer oil containing furaldehyde is withdrawn using a pipette which contains the first component (a) as described above. The withdrawn oil and first component (a) are then dispensed into a suitable container containing component (b) as discussed above. The third component (c) as described above is then added on top of the oil/first and second components mixture. The container is then capped and shaken. After about 60 seconds, the characteristic pink/red colour of the primary amine-furaldehyde reaction appears in the separated upper layer, above the oil/first and second component mixture.

The present invention provides a process for making the liquid containing the pink/red colour of the primary amine-furaldehyde reaction easily accessible for further use, by using a non-miscible petroleum product philic solvent in the second component with a sufficiently high specific gravity so that after the test is performed, the layer containing the said red/pink colour separates out on top of the oil/solvent layer, rather than below it where there is more interference. It is advantageous to have the pink/red colour layer separate on top where it is more clearly visible and less contaminated by oil and oxidation products than if the pink/red layer separates below, as in Orelup.

To estimate the 2-furaldehyde content, the intensity of the developed colour in the top layer is compared with colour standards that simulate the hue and intensity of colours from a 0.1 ppm to 1.5 ppm range of 2-furaldehyde concentration. The colour standards are supplied in association with the kit, or separately.

Reagent Packaging Kit

The first component (a) is placed on an absorbent substrate such as nylon fabric and is contained in a dispensing device such as a polyethylene disposable pipette.

The second component (b) is contained in a glass vessel such as a test tube fitted with a Teflon™ lined phenolic cap.

The third component (c) is contained in a dispensing device such as a polyethylene disposable pipette.

For a more complete understanding of the present invention, and to confirm the efficacy of the reagent and the method, reference is now made to the following specific examples illustrating the present novel three-component reagent for detecting furaldehyde in mineral oils.

EXAMPLE 1

About 3 mL of viscous oxidized transformer oil was withdrawn using the pipette that contains the first reagent component (a). The first component (a) and the transformer oil were then dispensed into the test tube containing the second component (b). The third reagent component (c) was then introduced on top of the oil/reagent components mixture and the tube was then capped and shaken. After 60 seconds, it was observed that the developed pink/red colour was removed by the third reagent and this layer, which was clear and bright, separated out on top of the lower dark oil and other reagents layer.

This described process was repeated five more times using the same transformer oil containing: 0.2, 0.3, 0.5, 0.8 and 1.0 ppm of furaldehyde respectively.

The same general results were obtained. However, it was noticed that the intensity of the pink/red colour in the top layer increased proportionately in accordance with the relative increase in furaldehyde content of the oil. The increased intensity of pink/red colour could be readily compared with a corresponding colour chart to thereby determine the concentration of furaldehyde.

The results of Example 1 demonstrate that the reagent of the invention is very sensitive and is more effective than conventional tests and can be used for semi-quantitative measurement. Furthermore, since the number of chemicals in each component is minimal, there is no dilution factor which decreases the sensitivity of the test.

Comparative Example

Prior to development of the test and formulation according to the invention with the diagnostic pink/red colour in the upper layer, numerous tests were conducted using acetic acid/aniline reagents, diluents such as ethanol and ethylene glycol, and water, for detecting furaldehyde in dark oxidized transformer oil. In such tests, the pink/red colour separated out into the lower layer, which was water, since the other fractions were lower specific gravity. We found, however, that the water layer at the bottom was not satisfactory because some of the yellowish and brownish oxidant products also separated into the lower water layer, thereby obscuring the correct pink/red colour in the lower water layer. Also, emulsion products formed by the oxidants tended to interfere with the indicator layer.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A reagent combination for determining extent of paper degradation in a transformer containing paper and oxidized transformer oil by detecting the presence and concentration of furaldehyde in the oxidized transformer oil consisting essentially of:

(a) a first component comprising about 0.1 mL of a primary amine selected from the group consisting of aniline, toluidine, anisidine, aminophenol and an amine; the first component being intended to be mixed with about 3 mL of the oxidized transformer oil;

(b) a second component comprising about 3 mL of about 15 to 33 volume percent of acetic acid alone, or in combination with citric acid; from about 67 to 85 volume percent of a halogenated hydrocarbon selected from the group consisting of dichloromethane, chloroform, carbontetrachloride, dichloroethane, trichloroethane, tetrachloroethane, trichloroethylene, tetrachloroethylene; about 4 weight to volume percent of salicylic acid; and about 1 volume percent of an anti-oxidant;

(c) a third component comprising about 1.5 mL of about 25 weight volume percent citric acid in distilled water; and (d) a calibrated colour standards medium illustrating colour intensity in proportion to concentration of furaldehyde and degree of paper degradation.

2. A reagent as claimed in claim 1 consisting essentially of aniline as the first component; acetic acid, tetrachloroethylene, salicylic acid and t-butyl hydroquinone as anti-oxidant, as the second component; and citric acid in distilled water as the third component.

3. A reagent kit for determining extent of paper degradation in a transformer by detecting the presence of furaldehyde in about 3 mL of oxidized transformer oil, said reagent kit comprising:

(a) a first sealed pipette containing about 0.1 mL of aniline;

(b) a vessel with a removable cap containing about 3 mL of about 15 (volume) percent of acetic acid, about 85 (volume) percent of tetrachloroethylene, about 4 (weight to volume) percent salicylic acid and about 1 (volume) percent compatible antioxidant;

(c) a second sealed pipette containing about 1.5 mL of about 25 (weight to volume) citric acid in distilled water; and (d) a calibrated colour standards medium illustrating colour intensity in proportion to concentration of furaldehyde and degree of paper degradation.

4. A reagent kit as claimed in claim 3 wherein the aniline in pipette (a) is absorbed in a substrate and the vessel (b) is a test tube with a Teflon lined plastic cap.

5. A reagent kit as claimed in claim 4 wherein the substrate is a nylon fabric and the pipettes (a) and (c) are disposable.

6. A process for determining extent of paper degradation in a transformer containing paper and oxidized transformer oil by detecting the presence of furaldehyde in the oxidized transformer oil comprising:

(a) withdrawing about 3 mL of the oxidized transformer oil into a first pipette containing about 0.1 mL of aniline;

(b) adding the 3 mL of oxidized transformer oil and the 0.1 mL of aniline contents of the first pipette to a transparent vessel containing about 3 mL of about 15 weight to volume percent of acetic acid and about 85 volume percent of tetrachloroethylene;

(c) adding to the vessel and its contents the contents of a second pipette containing 1.25 mL of about 25 weight to volume percent citric acid in distilled water;

(d) capping the vessel and shaking the contents of the vessel for a time sufficient to permit the contents to chemically react with one another, and subsequently ceasing the shaking to permit the contents to separate into layers with a distilled water layer on top and a transformer oil reagent layer on the bottom;

(e) observing the intensity of a pink/red colour characteristic of the presence and concentration of a furaldehyde complex in the water layer on top of the transformer oil reagent layer; and (f) comparing the intensity of the pink/red colour with the intensity of a colour on a calibrated colour standards medium which correlates colour intensity with concentration of furaldehyde and degree of paper degradation.

7. A process as claimed in claim 6 wherein the pipettes of steps (a) and (c) and the vessel of step (b) are sealed airtight prior to use.

8. A process as claimed in claim 6 wherein the aniline in step (a) is absorbed in a substrate in the first pipette.

9. A process as claimed in claim 6 wherein the calibrated colour standards medium has thereon hues and intensities of colours which correspond with concentrations of 0.1 ppm to 1.5 ppm of furaldehyde.

\* \* \* \* \*